United States Patent [19]
Prevatt

[11] Patent Number: 5,212,088
[45] Date of Patent: May 18, 1993

[54] **SPHEROPLAST FUSIONS OF *PHAFFIA RHODOZYMA* CELLS**

[75] Inventor: William D. Prevatt, Bartlesville, Okla.

[73] Assignee: Phillips Petroleum Company, Bartlesville, Okla.

[21] Appl. No.: 601,951

[22] Filed: Oct. 23, 1990

[51] Int. Cl.$^5$ .............................................. C12N 1/16
[52] U.S. Cl. .................. 435/255; 435/172.2; 435/911; 935/97
[58] Field of Search ............ 435/172.2, 255, 822, 435/911; 935/97

[56] References Cited

U.S. PATENT DOCUMENTS 4,239,782  12/1980  Cinquemani ........................... 426/2

FOREIGN PATENT DOCUMENTS

88/08025  10/1988  World Int. Prop. O. .
9001552   2/1990   World Int. Prop. O. .

OTHER PUBLICATIONS

O'Brien et al. Biochem. Soc. Trans. (18,2, 328-29) 1990 abstract only.
Evans et al. Arch Microbiol 148(1) 1987, 77-82.
Stewart Devel. in Industrial Microbiol. 29:1 1988.
An, et al., "Isolation of *Phaffia rhodozyma* Mutants with Increased Astaxanthin Content", Applied Environmental Microbiology, vol. 55, No. 1, pp. 116-124, Jan. (1989).
Johnson, et al., "The Yeast *Phaffia rhodozyma* as a Dietary Pigment Source for Salmonids and Crustaceans", J. Fish. Res. Board Can., vol. 34: 2417 (1977).
Johnson, et al., "Simple Method for the Isolation of Astaxanthin from the Basidiomycetous yeast *Phaffia rhodozyma*", Applied and Environmental Microbiology, vol. 35, No. 6, pp. 1155-1159 Jun. (1978).
Johnson, et al., "Astaxanthin Formation of the Yeast *Phaffia rhodozyma*", Journal of General Microbiology, vol. 115, pp. 173-183 (1979).
Johnson, et al., "*Phaffia rhodozyma* as an Astaxanthin Source in Salmonids Diets", Aquaculture, vol. 20, 123 (1980).
Lynch, "Plant Cell Wall Polymers", American Chemical Society, Chapter 44, 609, et seq.
Miller, et al., "*Phaffia*, a New Yeast Genus in the Deutersnycotins (Blastemycetes)", Int. J. Syst. Bact. vol. 26, 286 (1976).
Okagbue, et al., "Mixed Culture *Bacillus circulans* WL-12 and *Phaffia rhodozyma* in Different Carbon Sources: Yeast-wall Lytic Enzyme Production and Extractability of Astaxanthin", Biotechnology Letters, vol. 5, No. 11, 731-736 (1983).
Okagbue, "Autolysis of the Red Yeast *Phaffia rhodozyma*" a Potential Tool to Facilitate Extraction of Astaxanthin Biotechnology Letters, vol. 6, No. 4, 247-250 (1984).
Okagbue, et al., "Influence of Mixed Culture Conditions on Yeast-Wall Hydrolytic Activity of *Bacillus circulans* WL-12, etc.", Journal of Applied Bacteriology, vol. 59, 243-255 (1985).
Spencer, et al., "Yeast Genetics:Fundamental and Applied Aspects", Springer-Verlag.

*Primary Examiner*—Richard A. Schwartz
*Assistant Examiner*—John LeGuyader
*Attorney, Agent, or Firm*—Lucas K. Shay

[57] ABSTRACT

The present invention provides a process for the cell fusion of strains of *Phaffia rhodozyma* thereby providing novel strains of *Phaffia rhodozyma*.

8 Claims, No Drawings

SPHEROPLAST FUSIONS OF *PHAFFIA RHODOZYMA* CELLS

FIELD OF THE INVENTION

The present invention relates to a process for the fusion of *Phaffia rhodozyma* spheroplasts and novel strains of *Phaffia rhodozyma*.

BACKGROUND OF THE INVENTION

Astaxanthin (trans 3,3'-dihydroxy-4,4'-diketo-$\beta\beta'$-carotene also known as trans 3,3'-dihydroxy-$\beta,\beta'$-carotene-4,4'-dione) is an oxycarotenoid pigment widely distributed in plants and animals. It is a predominant oxycarotenoid pigment in crustaceans, and salmonids. Astaxanthin is also found in algae, yeast (such as *Phaffia rhodozyma*), bacteria and birds.

In commercial aquaculture it is desirable to add astaxanthin to the diet of salmonids and crustaceans to impart the distinctive pink coloration found in indigenous salmonids, crustaceans and birds. Imparting this distinctive pink coloration to salmonids and crustaceans produced by commercial aquaculture is believed to be important in encouraging consumer acceptance of salmonids and crustaceans produced through aquaculture. Currently no economical source for astaxanthin exists.

One potential source of aztaxanthin for aquacultural purposes is the yeast *Phaffia rhodozyma*. *Phaffia rhodozyma* has been recognized, since its classification as a yeast species having a high astaxanthin content ($\sim 85\%$ of its carotenoid pigment is astaxanthin, N. W. Miller, et al. *Int. J. Syst. Bacteriol.*, Vol. 26, p. 286 (1976). Use of this yeast as a dietary supplement in salmonid and crustacean diets has also been explored by Eric A. Johnson and other researchers since the early 1980's.

The development of *Phaffia rhodozyma* as a commercial source of astaxanthin has been hampered by the absence of strains of *Phaffia rhodozyma* which produce high levels of astaxanthin. The strains of *Phaffia rhodozyma* currently available generally produce from 30 to 2000 micrograms per gram of cell mass. Unfortunately the strains of *Phaffia rhodozyma* which are high astaxanthin producer exhibit extremely slow growth rates which render them unsuitable for commercial fermentation. Thus, it would be very advantageous to develop strains of *Phaffia rhodozyma* which produce high levels of astaxanthin and desirable growth rates (thereby providing higher overall yields).

Unfortunately the only method currently available for improving *Phaffia rhodozyma* strains is through repeated rounds of mutagenesis. However, repeated rounds of mutagenesis produces *Phaffia rhodozyma* strains with numerous mutations deleterious to the commercial fermentation of these strains. Thus improving *Phaffia rhodozyma* strains becomes increasingly difficult with each successive round of mutagenesis. This problem cannot be solved by utilizing classical mating techniques because sexual reproduction is unknown in *Phaffia rhodozyma*. Spheroplast fusion techniques could offer an alternative to classical mating techniques as a method for improving *Phaffia* strains, if a technique could be developed to generate *Phaffia rhodozyma* spheroplasts. However, *Phaffia rhodozyma* has an incredibly tough cell wall which has prevented researchers from being able to produce *Phaffia* spheroplasts suitable for cell fusions.

Thus, it would be advantageous to develop new strains of *Phaffia rhodozyma* which produce higher yields of astaxanthin.

It would also be advantageous to develop a process to produce *Phaffia rhodozyma* spheroplasts suitable for use in cell fusions.

It would further be useful to develop a process for fusing spheroplasts of *Phaffia rhodozyma*.

Thus it is an object of the present invention to provide strains of *Phaffia rhodozyma* which produce high yields of astaxanthin.

It is a further object of the present invention to provide a process for producing *Phaffia rhodozyma* spheroplasts suitable for use in cell fusions.

It is yet another object of the present invention to provide a process for fusing spheroplasts of *Phaffia rhodozyma*.

Other aspects, objects and several advantages of this invention will be apparent from the instant specification.

SUMMARY OF THE INVENTION

In accordance with the present invention I have discovered a stable fusion strain of *Phaffia rhodozyma* which produces in the range of from about 1430 $\mu$g/g to about 1660 $\mu$g/g of astaxanthin, and from about 2350 $\mu$g/g to about 2950 $\mu$g/g of total carotenoids and provides a yield of at least 24 percent on a dry weight basis when cultivated under suitable growth conditions in a shake flask with a productivity of in the range of from about 4500 $\mu$g/l to about 8600 $\mu$g/l based on a 5 day shake flask assay wherein the strain is cultivated under suitable conditions to facilitate near optimum growth of said strain.

In accordance with the present invention, also I have discovered a process for producing spheroplasts of *Phaffia rhodozyma* suitable for use in cell fusions comprising contacting a viable *Phaffia rhodozyma* cell having a cell wall, under suitable conditions with an effective amount of a suitable digestive enzyme preparation obtained from *Trichoderma harzianium*, to facilitate the removal of said cell wall and the formation of a viable *Phaffia rhodozyma* spheroplast.

In another embodiment of the present invention, I have also discovered a process for the fusion of *Phaffia rhodozyma* cells comprising (a) contacting viable *Phaffia rhodozyma* cells having cell walls, under suitable conditions with an effective amount of a suitable digestive enzyme preparation obtained from *Trichoderma harzianium*, to facilitate the removal of said cell wall and the formation of viable *Phaffia rhodozyma* spheroplasts;

(b) treating said spheroplasts in a manner which facilitates the fusion of the cell walls of one or more spheroplasts.

DETAILED DESCRIPTION OF THE INVENTION

Cell fusion of *Phaffia rhodozyma* strains provides a process for restoring vigorous growth characteristics to high astaxanthin producing strains of *Phaffia rhodozyma* with poor growth characteristics. The discovery of a process to form Phaffia cell fusions thus provides a easier way to continuously improve Phaffia cell strains. The fusion of *Phaffia rhodozyma* cell strains was not previously possible because of the inability of researchers to remove the tough cell walls characteristic of *Phaffia rhodozyma* cells. I have discovered that spheroplasts of *Phaffia rhodozyma* can effectively be formed utilizing an enzyme preparations obtained from the fungus *Trichoderma harzianium*. Utilizing these preparations it is possible for the first time to form *Phaffia rhodozyma* spheroplasts and perform cell fusions with these spheroplasts.

Suitable strains of *Trichoderma harzianium* are publicly available from the American Type Culture Collection, 12301 Parklawn Drive, Rockville, Md. (such as ATCC 64986). These strains may be cultured and stimulated to produce digestive enzymes by submerged culture fermentation as is known by those skilled in the art. A suitable source of *Trichoderma harzianium* digest enzyme preparations is Novo Enzymes SP-299-Mutanase TM and Novozyme TM SP-234 a purified form of Mutanese TM.

Viable *Phaffia rhodozyma* cells should be treated with an effective amount of *Trichoderma harzianium* digestive enzyme preparation to result in the substantial removal of the *Phaffia rhodozyma* cell walls while retaining the viability of a portion of the spheroplasts formed by this process. Generally cell wall removal of the *Phaffia rhodozyma* can be determined utilizing suitable techniques known to those skilled in the art including microscopic examination, or by photometric monitoring of turbidity, or by plating. Presently it is preferred to follow removal of the cell wall by photometrically monitoring turbidity. Typically a sample of *Phaffia rhodozyma* cells will be placed in an aqueous solution with the digestive enzyme preparation and the turbidity of the solution monitored until a significant drop in the turbidity is observed. The drop in turbidity will generally correspond to a portion of the cells being lysed by the digestive enzyme preparation. Generally the amount of digestive enzyme preparation per 100 grams/liter of aqueous *Phaffia rhodozyma* will be dependent on the temperature, pH and condition of the *Phaffia rhodozyma* cells employed. As a guideline it is recommended that the amount of *Trichoderma harzianium* utilized range from about 0.5 units to about 5.0 units of *Trichoderma harzianium* digestive enzyme preparation per 100 grams/liter of *Phaffia rhodozyma* cells. Currently, it is preferred that in the range of from 1 to 2 units of *Trichoderma harzianium* digestive enzyme preparation per 100 grams/liter of *Phaffia rhodozyma* cells be utilized. A unit is defined as the amount of *Trichoderma harzianium* digestive enzyme which will provide the equivalent amount of released astaxanthin as the acetone extraction described in Example V, on a sample of aqueous *Phaffia rhodozyma* with a density of 100 grams/liter, removed while in a logarithmic growth phase, when the digestive enzyme is contacted with the *Phaffia rhodozyma* cells at 22° C., and pH 4.5 and allowed to incubate for 24 hours.

Temperature at which *Phaffia rhodozyma* cells are contacted with the digestive enzyme preparation may be any temperature which allows the digestive enzyme preparation to digest *Phaffia rhodozyma* cell walls. Generally temperatures should range from about 0° C. to about 60° C. Preferred for the practice of this invention are temperatures in the range of from about 20° C. to about 30° C.

The pH at which *Phaffia rhodozyma* cells are contacted with the digestive enzyme preparation may be any suitable pH which permits the digestive enzyme preparation to digest *Phaffia rhodozyma* cell walls. Generally the pH at which *Phaffia rhodozyma* cells are contacted with the digest enzyme preparation should range of from about pH 4.0 to about pH 5.5 and preferably be in the range of from about pH 4.5 to about pH 5.0.

*Phaffia rhodozyma* cells may be contacted with the digestive enzyme preparation derived from *Trichoderma harzianium* at any time during the life cycle of *Phaffia rhodozyma*. However, it is preferred that the *Phaffia rhodozyma* cells be contacted with the digestive enzyme preparation after the *Phaffia rhodozyma* cells have reached late logarithmic growth phase or early stationary phase, preferably in the range of from about 1 generation to about 10 generations after a logarithmic growth phase and most preferably in the range of from about 2 generations to about 4 generations.

The mixing of an aqueous suspension of *Phaffia rhodozyma* cells and the *Trichoderma harzianium* digestive enzyme preparation may be accomplished by any suitable means. Mixing is generally accomplished by contacting a dried digestive enzyme preparation with an aqueous *Phaffia rhodozyma* fermentation broth or aqueous cell suspension and admixing said dry digestive enzyme preparation into solution.

The digestive enzyme preparation derived from *Trichoderma harzianium* may be contacted with viable *Phaffia rhodozyma* cells for an amount of time effective to result in the substantial removal of cell walls of the *Phaffia rhodozyma* cells. The amount of time depends on the cell concentration, pH, temperature and units of digestive enzyme preparation utilized. Generally the time of contacting the *Phaffia rhodozyma* cells with the digestive enzyme preparation derived from *Trichoderma harzianium* should be in the range of about 1 hour to about 4 hours and preferably the time of contacting will be about 2 hours.

*Phaffia rhodozyma* Spheroplast Fusion Techniques

Once the spheroplasts are formed, standard yeast fusion techniques may be used to fuse the *Phaffia rhodozyma* spheroplasts. Yeasts fusion techniques are well know to those skilled in the art. One suitable technique is described in Example I. The following discussion of *Phaffia rhodozyma* fusion is illustrative of techniques which may be utilized in *Phaffia rhodozyma* spheroplast fusion.

After the cell walls have been substantially removed, the viable spheroplasts so formed should be collected and removed from contact with the digestive enzyme preparation. Suitable separatory techniques for removing the cell from the digestive enzyme preparation include but are not limited to centrifugation or filtration. The suitable separatory techniques used to separate the spheroplasts from contact with the digestive enzyme preparation should facilitate the continued viability of the spheroplasts. The *Phaffia rhodozyma* spheroplasts may be optionally washed in an isotonic solution to facilitate the complete removal of the digestive enzyme preparation. The *Phaffia rhodozyma* spheroplasts will then be recovered from the isotonic wash solution by suitable separator techniques.

Following the removal of the *Phaffia rhodozyma* cell wall, the spheroplasts so formed must be treated with care to avoid rupturing the cell membrane. To avoid rupturing the spheroplast, it is advisable that the spheroplasts be maintained in a substantially isotonic solution until after the fusion of the spheroplasts is complete and the cell wall has regenerated. Isotonic solution can be formed with a variety of buffers and water soluble nontoxic agents including but not limited to glucose, D-mannitol, D-sorbitol, sucrose, or potassium chloride. It is currently preferred that the isotonic solution have a concentration of solutes (which includes at least the buffer and the soluble nontoxic agents) in the range of from about 0.5M to about 3M, preferred is a concentration of about 1M.

To induce spheroplast fusion, the spheroplasts should be treated with an agent which promotes cell membrane to cell membrane adhesion and fusion such as polyethylene glycol. The spheroplasts should be placed in contact with the polyethylene glycol for a limited period of time because of its toxicity to the spheroplasts. Generally the concentration of polyethylene glycol contacted with the spheroplasts should be sufficient to induce fusion within a reasonable time but of a low enough concentration to avoid excessive spheroplast mortality. It is currently preferred that the polyethylene glycol be provided in a substantially isotonic solution at a concentration from in the range of about 100 grams/liter to about 300 grams/liter, it is most preferred that the concentration of polyethylene glycol be about 200 grams/liter of the isotonic solution contacted with the spheroplasts. The length of time for which the polyethylene glycol should be contacted with the spheroplasts will depend on the number of cell per unit volume and the degree of fusion desired (the longer the period of contacting and the higher the cell concentration per unit volume, the greater the likelihood that multiple fusions of three or more cells will occur). For the practice of the present invention it is currently preferred that the polyethylene glycol be contacted with the spheroplasts in the range of from about 10 minutes to about 20 minutes and most preferably for about 15 minutes. The fused spheroplasts should then be washed with an isotonic solution and recovered by centrifugation.

After the fused spheroplasts have been recovered the fused cells will need to be placed under suitable conditions to facilitate the regeneration of the fused *Phaffia rhodozyma* cell wall. One suitable technique for facilitating the regeneration of the *Phaffia rhodozyma* cell wall is to plate the fused spheroplasts on plates in an isotonic top agar. Plating *Phaffia rhodozyma* spheroplasts requires that a few precautions be taking. Since *Phaffia rhodozyma* cells are temperature sensitive, the top agar should have either a low melting point or be applied in a very thin layer which will cool quickly. Currently it is preferred that the top agar be applied in a very thin layer because it is desirable that the colonies which form in the agar penetrate the top agar and come in contact with air. Only those colonies which penetrate the top agar and contact the air will exhibit the carotenoid coloration characteristic of *Phaffia rhodozyma* cells (this facilitates easy identification of the colonies of interest). It also preferred for the practice of the present invention that the bottom or support layer of agar on to which the top agar is poured be isotonic. The colonies formed after fusion may be isolated and further screened for astaxanthin production, strain stability and growth characteristics using standard microbiological techniques.

The following table demonstrates the strain improvements possible utilizing spheroplast fusion between selected strains of *Phaffia rhodozyma* to provide significantly improved fusion strains of *Phaffia rhodozyma*. These fusion strains exhibit significantly improved astaxanthin production and improved growth characteristics compared to the parent strain, PC 8055.

TABLE I

| Phillips Culture Collection No. | NRRL No. | Astaxanthin[1] µg/l |
|---|---|---|
| PC 8055* | Y-10291 | 1260 |
| PC 8166[2] | Y-18730 | 8200 |
| PC 8168[2] | Y-18731 | 7636 |
| PC 8170[2] | Y-18732 | 7706 |
| PC 8239[2] | Y-18733 | 8568 |
| PC 8243[2] | Y-18734 | 7661 |

*The parent strain was 67-210, also known as PC 8055, which is deposited and accessible to the public from the United States Department of Agriculture, Agricultural Research Service, Northern Regional Research Center located in Peoria, Illinois under accession number NRRL Y-10291.

[1] Astaxanthin content was determined by the method described in Example II. The strains were grown under the conditions described in Example II.

[2] The isolated substantially pure strains of *Phaffia rhodozyma* with corresponding NRRL numbers have been deposited with the United States Department of Agriculture, Agricultural Research Service, Northern Regional Research Center, 1815 North University Street, Peoria, Illinois 61604, under the terms of the Budapest Treaty.

With the inventive *Phaffia rhodozyma* strains PC8166, PC8168, PC8170, PC8239, and PC8243, the increase in astaxanthin productivity is due to increased levels of astaxanthin (trans 3,3'-dihydroxy-4,4'-diketo-$\beta,\beta'$-carotene also know as trans-3,3'-dihydroxy-$\beta,\beta$-carotene-4,4'-dione) production. The increased astaxanthin productivities of these strains under suitable growth conditions is in the range of from about 4500 µg/l to about 8600 µg/l of astaxanthin when cultivated in a shake flask. Preferably the astaxanthin productivity of these strains under the conditions described above will be in the range of from about 5600 µg/l to about 8600 µg/l and most preferably will range from about 7600 µg/l to about 8600 µg/l of astaxanthin. The increased astaxanthin productivities of these strains also will result in an increased level of astaxanthin of from in the range of from about 1430 µg/g to about 1660 µg/g of astaxanthin on a dry weight basis when cultivated in shake flask. Preferably the level of astaxanthin produced will be in the range of from about 1515 µg/g to about 1660 µg/g of astaxanthin on a dry weight basis when cultivated in shake flask. The increased productivity observed will also translate into increased total carotenoid productivity in the range of from about 2350 µg/g to about 3000 µg/g of carotenoid on a dry weight basis. Preferably the amount of carotenoid produced will be in the range of from about 2460 µg/g to about 2950 µg/g of carotenoid on a dry weight basis.

Suitable growth conditions in a shake flask are defined as the conditions necessary to provide the maximum specific growth rate for the *Phaffia rhodozyma* strain being cultivated in a shake flask which is being vigorously agitated after 5 days of growth. Suitable growth conditions for the *Phaffia rhodozyma* strains of the present invention in a shake flask include utilizing Shake Flask Assay Growth Medium as defined in the Examples of this application and cultivating the strain at between 20° C. to 22° C. with vigorous shaking (as set forth in Example II).

Fermentation

*Phaffia rhodozyma* is a relatively new organism for use in industrial fermentation. Several workers in the area of *Phaffia rhodozyma* fermentation have observed that alcohol or aldehydes will accumulate in levels toxic to Phaffia if an excess carbon-energy source in the form of sugar is provided. This has led these workers to suggest growing *Phaffia rhodozyma* cells under conditions where the amount of carbon-energy source provided limits growth conditions. However, *Phaffia rhodozyma* responds to carbon-energy source limitation by producing lower astaxanthin yields and releasing compounds which cause excessive foaming in the fermentation vessel. The presence of these foam-causing compounds necessitates the use of antifoamants to avoid fermentation vessel overflow. Unfortunately the utilization of antifoamants can reduce the per cell astaxanthin yields.

We, however, have discovered that by maintaining a measurable excess of at least one suitable carbon-energy source in the fermentation broth containing the aqueous *Phaffia rhodozyma* cells and nutrients that alcohol and aldehyde production can be easily controlled and foaming avoided. Additionally the presence of a measurable excess of carbon-energy source also results in increased cell growth rates and astaxanthin yields.

Particularly important in improving astaxanthin and cell yields is the maintenance of a measurable excess of at least one suitable carbon-energy source while the *Phaffia rhodozyma* cells are in the transition phase between inoculation and the logarithmic growth phase. Preferably the *Phaffia rhodozyma* cells will be contacted with a measurable excess of at least one suitable carbon-energy source from the transition phase after inoculation through a substantial portion of the logarithmic growth phase.

The measurable excess of at least one suitable carbon-energy source provided should be an effective amount to avoid excessive foam formation during the fermentation of *Phaffia rhodozyma* and also not result in the generation of growth repressing or toxic levels of alcohol or aldehyde. Preferably the measurable excess of at least one carbon-energy source detectable in the fermentation broth consisting of the aqueous *Phaffia rhodozyma* cells and nutrients, will range from about 1.0 gram/liter to about 20 grams/liter and most preferably it will range from about 1.0 grams/liter to about 5.0 grams/liter. The amount of measurable excess of at least one suitable carbon-energy source in the fermentation broth should be controlled to avoid excess alcohol or aldehyde production. Preferably the amount of alcohol in the fermentation broth should range from about 0.0 grams/liter to about 3.0 grams/liter. Preferably the amount of aldehyde present in the fermentation broth will range from about 0.0 grams/liter to about 0.1 grams/liter.

The fermentation of *Phaffia rhodozyma* can be conducted in a aqueous continuous or batch-fed manner, utilizing a variety of carbon-energy sources and/or nutrient sources. Suitable carbon-energy sources for growing *Phaffia rhodozyma* include but are not limited to the carbon-energy source selected from the group consisting of succinate, furamate, malate, pyruvate, glucose, sucrose, fructose, maltose, corn syrup, hydrolyzed starch and combinations of any two or more thereof. Preferred carbon-energy sources for growing *Phaffia rhodozyma* are carbon-energy sources selected from the group consisting of succinate, glucose, and combinations thereof. A suitable nutrient or media source for *Phaffia rhodozyma* would include at least one nitrogen source, at least one phosphate source, at least one source of minerals such as iron, copper, zinc, magnesium, manganese, calcium, and other trace elements, and vitamins (such as biotin, pantothenic acid and thiamine) as required.

Suitable sources of at least one carbon-energy source and nutrients can be obtained from a variety of sources or may consist of a single source such as cane molasses. However, preferred are at least one carbon-energy source and/or nutrient sources which have a defined character. At least one carbon-energy source and nutrient composition which has proven particularly effective is set forth in Table 2.

TABLE 2

| Carbon-Energy Source and Nutrients | |
|---|---|
| Component per Liter of Water | |
| Glucose | 10–100 (g/l) |
| $H_3PO_4$ (85%) | 0.16–2.7 (ml/l) |
| $CaSO_4.2H_2O$ | 0.011–0.8 (g/l) |
| $K_2SO_4$ | 0.171–1.3 (g/l) |
| $MgSO_4.7H_2O$ | 0.140–1.56 (g/l) |
| KOH | 0.047–0.35 (g/l) |
| Biotin | 0.006–0.044 (mg/l) |
| Thiamine | 0.12–9.8 (mg/l) |
| [1]Yeast extracts | 1.2–6.0 (g/l) |
| [2]Minerals and Trace metals | 0.118–9.8 (ml/l) |

[1]Yeast extract is Amberex 1003 which is available from and a trademark of Universal Foods Corporation, Milwaukee, Wisconsin.
[2]Minerals and trace metals are $FeSO_4.7H_2O$ 65.0 g/l, $CuSO_4.5H_2O$ 6.0 g/l, $ZnSO_4.7H_2O$ 20 g/l, $MnSO_4$ 3.0 g/l and $H_2SO_4$ 5.0 ml/l The yeast extracts utilized in the present invention include but are not limited to yeast extracts selected from the group consisting of Amberex ™ 1003 (Universal Foods Corporation) and Bacto ™ Yeast Extract (Difco Laboratories Incorporated).

Trace metals utilized in the present invention are those trace metals generally utilized in yeast growth provided in an amount sufficient to not limit the growth rate or astaxanthin production of *Phaffia rhodozyma* which include but are not limited to trace metals selected from the group consisting of cobalt and molybdenum.

The fermentation temperature should generally range from about 18° C. to about 22° C. and preferably should be about 20° C.

The dissolved oxygen content in the fermentation vessel where the fermentation is conducted in a batch-fed manner may range from about 10% to about 80% of saturation and preferably will range from about 30% to about 60% of saturation. The dissolved oxygen content in a continuous fermentation should range from about 70% to about 100% of saturation and preferably be in the range of from about 70% to about 80% of saturation. The pH at which the *Phaffia rhodozyma* cells are cultivated should range from about 3.0 to about 5.5 and preferably the pH will range from about 4.5 to about 5.4.

After the fermentation broth containing the *Phaffia rhodozyma* cells has reached a desired cell density or astaxanthin content, the cell mass may be harvested. It is preferred that the *Phaffia rhodozyma* culture be held in a stationary phase for from the range of from about 4 to about 24 hours and most preferably in the range of from about 8 to about 12 hours to increase the astaxanthin yield.

However, *Phaffia rhodozyma* should not be maintained for extended periods of time in a stationary phase because the *Phaffia rhodozyma* cells will form tough cell walls which will be detrimental to cell breakage.

Cell Breakage

Salmonids, crustaceans and birds cannot utilize astaxanthin from unbroken *Phaffia rhodozyma* cells. To utilize *Phaffia rhodozyma* as a dietary source of astaxanthin, the cell walls of *Phaffia rhodozyma* must be disrupted by physical, chemical, mechanical, or enzymatic means. *Phaffia rhodozyma* cell walls are very resistant to normal lysis protocols. For example, bead milling will only release ~40% of the astaxanthin present in *Phaffia rhodozyma* cells after three passes through a bead mill (more passes through a bead mill will not substantially increase the release of astaxanthin). A Gaulin Press will release ~95% of the astaxanthin present in *Phaffia rhodozyma* but only after three passes through the Gaulin Press (which is time consuming and requires a significant capital expenditure). Enzymatic lysis of *Phaffia rhodozyma* also had not proven to be economical or effective in releasing astaxanthin from *Phaffia rhodozyma* until the discovery of the present invention.

Applicants have discovered that an effective amount of a digestive enzyme preparation from the fungus *Trichoderma harzianium* is capable of digesting the cell wall of *Phaffia rhodozyma*. This results in an almost complete availability of the astaxanthin present in *Phaffia rhodozyma* as determined by comparison to acetone extraction which is described in Example V.

Suitable strains of *Trichoderma harzianium* are publicly available from the American Type Culture Collection, 12301 Parklawn Drive, Rockville, Md. (such as ATCC 64986). These strains may be cultured and stimulated to produce digestive enzymes by submerged culture fermentation as is known by those skilled in the art. One suitable source of *Trichoderma harzianium* digest enzyme preparations is Novo Enzymes SP-299-Mutanase.

*Phaffia rhodozyma* cells containing astaxanthin should be treated with an effective amount of *Trichoderma harzianium* digestive enzyme preparation to result in the availability of substantially all the astaxanthin contained therein. Generally the amount of digestive enzyme preparation per 100 grams/liter of aqueous *Phaffia rhodozyma* will be dependent on the temperature, pH and condition of the *Phaffia rhodozyma* cells employed. as a guideline it is recommended that the amount of *Trichoderma harzianium* utilized range from about 0.2 units to about 10.0 units of *Trichoderma harzianium* digestive enzyme preparation per 100 grams/liter of *Phaffia rhodozyma* cells. A unit is defined as the amount of *Trichoderma harzianium* digestive enzyme which will provide the equivalent amount of released astaxanthin as the acetone extraction described in Example V, on a sample of aqueous *Phaffia rhodozyma* with a density of 100 grams/liter, removed while in a logarithmic growth phase, when the digestive enzyme is contacted with the *Phaffia rhodozyma* cells at 22° C., and pH 4.5 and allowed to incubate for 24 hours.

Temperature at which *Phaffia rhodozyma* cells are contacted with the digestive enzyme preparation may be any temperature which allows the digestive enzyme preparation to digest *Phaffia rhodozyma* cell walls. Generally temperatures should range from about 0° C. to about 60° C. Preferred for the practice of this invention are temperatures in the range of from about 20° C. to about 30° C.

The pH at which *Phaffia rhodozyma* cells are contacted with the digestive enzyme preparation may be any suitable pH which permits the digestive enzyme preparation to digest *Phaffia rhodozyma* cell walls. Generally the pH at which *Phaffia rhodozyma* cells are contacted with the digest enzyme preparation should be in be in the range of from about pH 4.0 to about pH 5.5 and preferably be in the range of from about pH 4.5 to about pH 5.0.

*Phaffia rhodozyma* cells containing astaxanthin may be contacted with the digestive enzyme preparation derived from *Trichoderma harzianium* at any time during the life cycle of *Phaffia rhodozyma*. However, it is preferred that the *Phaffia rhodozyma* cells be contacted with the digestive enzyme preparation as soon as possible after the *Phaffia rhodozyma* cells have been in a logarithmic growth phase, preferably in the range of from about 0 hours to about 72 hours after a logarithmic growth phase and most preferably in the range of from about 0 hours to about 24 hours.

The mixing of an aqueous suspension of *Phaffia rhodozyma* cells and the *Trichoderma harzianium* digestive enzyme preparation may be accomplished by any suitable means. Mixing is generally accomplished by contacting a dried digestive enzyme preparation with an aqueous *Phaffia rhodozyma* fermentation broth or aqueous cell suspension and admixing said dry digestive enzyme preparation into solution.

The digestive enzyme preparation derived from *Trichoderma harzianium* may be contacted with *Phaffia rhodozyma* cells which contain astaxanthin for an amount of time effective to result in the substantial release of astaxanthin present in the *Phaffia rhodozyma* cells as compared to acetone extraction described in Example V.A. The amount of time depends on the cell concentration, pH, temperature and units of digestive enzyme preparation utilized. Generally the time of contacting the *Phaffia rhodozyma* cells with the digestive enzyme preparation derived from *Trichoderma harzianium* should be in the range of about 12 hours to about 24 hours and preferably the time of contacting will be about 24 hours.

Drying of *Phaffia rhodozyma* Cells

The *Phaffia rhodozyma* cells after having been broken or digested in a manner which renders the astaxanthin contained therein available for use as a dietary pigment supplement can be dried. Drying may be performed using a fluidized bed drier, drum drier, or spray drier. Spray drying is presently preferred because of the short exposure time to high temperatures which could possibly degrade the astaxanthin present.

After drying, the resultant product will be a powdery yeast material which may be recovered by any suitable means such as a cyclone, and further handled for use in feed, storage, or shipping.

EXAMPLES

| Strains | |
|---|---|
| *Phaffia rhodozyma* PC 8055 | NRRL Y-10921 |
| *Phaffia rhodozyma* PC 8166 | NRRL Y-18730 |
| *Phaffia rhodozyma* PC 8168 | NRRL Y-18731 |
| *Phaffia rhodozyma* PC 8170 | NRRL Y-18732 |
| *Phaffia rhodozyma* PC 8239 | NRRL Y-18733 |
| *Phaffia rhodozyma* PC 8243 | NRRL Y-18734 |
| Shake Flask Assay Growth Medium | |
| glucose | 20.0 g/L |
| $KH_2PO_4$ | 10.0 g/L |
| $K_2HPO_4$ | 5.0 g/L |
| $(NH_4)_2SO_4$ | 1.0 g/L |
| calcium pantothenante | 0.0200 g/L |
| pyridoxine.HCl | 0.0125 g/L |
| thiamine.HCl | 0.0100 g/L |
| nicotinic acid | 0.0100 g/L |
| $CaCl_2.2H_2O$ | 0.01 g/l |
| $ZnSO_4.7H_2O$ | 0.0070 g/L |
| Hemin | 0.005 g/l |
| $CuSO_4.5H_2O$ | 0.0006 g/L |
| $MnSO_4.2H_2O$ | 0.0002 g/L |
| biotin | 0.00015 g/L |
| Mazu DF 37C antifoam | 10.0 drops/L |

-continued

| Strains | |
|---|---|
| Modified YMA Medium | |
| Bacto Yeast Extract | 3.0 g/l |
| Difco Malt Extract | 3.0 g/l |
| Dextrose | 20.0 g/l |
| Agar | 20.0 g/l |
| Water | 1.0 L |
| | (per liter of water) |
| Bio Lafitte Media | |
| $H_3PO_4$ (85%) | 14.5 ml |
| $CaSO_4.2H_2O$ | 0.60 g |
| $K_2SO_4$ | 9.12 g |
| $MgSO_4.7H_2O$ | 7.60 g |
| KOH | 2.60 g |
| glucose | 40.0 g |
| yeast extract | 20.0 g |
| trace metals[1] | 4.0 ml |
| biotin | 8 mg |
| thiamine | 8 mg |
| MAZU DF 37C antifoam | 12 drops |
| [1]trace metals contain (YTM-4): | |
| $FeSO_4.7H_2O$ | 16.25 g/250 ml |
| $CuSO_4.5H_2O$ | 1.50 g/250 ml |
| $ZnSO_4.7H_2O$ | 5.00 g/250 ml |
| $MnSO_4.H_2O$ | 0.75 g/250 ml |
| $H_2SO_4$ | 1.25 g/250 ml |

EXAMPLE I

Fusion of Spheroplasts

Cultures of *Phaffia rhodozyma* were prepared in 100 ml of modified YMA broth and allowed to incubate for five days at 20° C. 2.5 ml (total volume) of equivalent Klett units were mixed for each culture in a sterile centrifuge tube and pelleted at 12,000 g at 20° C. for 10 min. The pellet was washed 2× with sterile 100 mM phosphate buffer (pH 4.0) containing 1M sorbitol and then resuspended in 25 ml of the same buffer with sorbitol. The resulting solution was split into two 10 ml aliquots. To one aliquot was added 0.5 ml of 10 mg/ml Mutanase (SP299) and both aliquots were incubated at room temperature for 2 hours followed by chilling on ice. Cell wall removal was monitored by adding 0.1 ml of each aliquot to 4.9 ml of 5% SDS and measuring the absorbance at 600 nm ($A_{600}$), followed by observing a portion of each aliquot under a light microscope.

Spheroplasts were pelleted from each aliquot by centrifugation at 120 g at 20° C. for 10 min and washed 2× with 10 ml of sterile 100 mM phosphate buffer (pH 4.0) containing 1M sorbitol. Each aliquot was gently resuspended in 1.0 ml of 100 mM phosphate buffer (pH 4.0) containing 1M sorbitol. 9 ml of sterile 20% polyethylene glycol-3350 in 100 mM phosphate buffer (pH 4.0) was added and incubated at room temperature for 15 min.

The spheroplasts were then pelleted at 120 g for 10 min at 20° C., and the PEG was removed using sterile pasteur pipetes. The spheroplasts were resuspended in 10 ml of modified YM broth containing 1M sorbitol and incubated for 30 min at room temperature. 0.1 ml of each aliquot was pipetted onto the surface of 20 modified YMA plates containing 1M sorbitol. 10 ml of modified YM containing 1M sorbitol and 1% agar (which had been held at 42° C.) was added to the surface of the plates. The cells were mixed into the top agar by gentle swirling, and the plates were then incubated at room temperature for 5 to 10 days, single colonies wee picked and plated on modified YMA plates, incubated at 20° C. for 5 days and assayed for astaxanthin content.

EXAMPLE II

Astaxanthin Production in Fusion Strains

The following Table denotes the fusion strains generated in Example I and the levels of astaxanthin produced by each strain, when grown for 5 days in a shake flask. Each strain was grown in a 100 ml modified YM shake flask, which was innoculataed with a loopful of *Phaffia rhodozyma* culture from a 5-10 day old modified YMA plate. The shake flask was incubated 5 days on an orbital shaker (10 cm strokes at 200 rpm) at 20° C. 10 ml of the shake flask culture was innoculated into 1000 ml of Shake Flask Assay Medium in a 2.8 L tripple-baffled Fernbach flask. Samples were analyzed for washed cell dry weight, astaxanthin content (HPLC), and total carotenoid content (HPLC) after 5 days on an orbital shaker (10 cm strokes at 200 rpm) at 20° C. Cell yield (based on total glucose concentration) is calculated using the following formula:

$$\frac{\text{Washed cell dry weight (g/L)}}{20 \text{ g/L (glucose concentration)}} \cdot 100\%$$

Volumetric astaxanthin productivity was calculated using the following formula:

Washed cell dry weight (g/L) × Astaxanthin (μg/g of cells)

TABLE I

Phaffia Fusion Strains

| PC # | DESCRIPTION | % YIELD[1] | ASTAXANTHIN[2] (PPM) | CAROTENOIDS[2] (PPM) | PRODUCTIVITY[3] μg/K |
|---|---|---|---|---|---|
| 8166 | 8055 × 8059 × 8117 #27 (stable) | 24.7 | 1660 | 2775 | 8200 |
| 8055 | PARENT | 35.0 | 180 | 495 | 1260 |
| 8059 | PARENT | 35.0 | 535 | 915 | 3745 |
| 8117 | PARENT (Unstable) | 19.5 | 1960 | 3245 | 7644 |
| 8168 | 8055 × 8059 × 8117 #7 (Stable) | 25.2 | 1515 | 2460 | 7636 |
| 8055 | PARENT | 35.0 | 180 | 495 | 1260 |
| 8059 | PARENT | 35.0 | 535 | 915 | 3745 |
| 8117 | PARENT (Unstable) | 19.5 | 1960 | 3245 | 7644 |
| 8170 | 8055 × 8117 #23 (Stable) | 25.1 | 1535 | 2490 | 7706 |
| 8055 | PARENT | 35.0 | 180 | 495 | 1260 |
| 8117 | PARENT (Unstable) | 19.5 | 1960 | 3245 | 7644 |
| 8239 | 8055 × 8059 × 8146 × 8147 × 8148 #60 (Stable) | 28.0 | 1530 | 2950 | 8568 |
| 8055 | PARENT | 35.00 | 180 | 495 | 1260 |
| 8059 | PARENT | 35.0 | 535 | 915 | 3745 |
| 8146 | PARENT | 22.1 | 1725 | 2715 | 7625 |
| 8147 | PARENT (Unstable) | 22.8 | 1070 | 1675 | 4879 |
| 8148 | PARENT (Unstable) | 21.1 | 1275 | 1965 | 5381 |

TABLE I-continued

| | | Phaffia Fusion Strains | | | |
|---|---|---|---|---|---|
| PC # | DESCRIPTION | % YIELD[1] | ASTAXANTHIN[2] (PPM) | CAROTENOIDS[2] (PPM) | PRODUCTIVITY[3] μg/K |
| 8243 | 8216 × 8059 #41 (Stable) | 28.5 | 1430 | 2350 | 7661 |
| 8059 | PARENT | 35.0 | 535 | 915 | 1260 |
| 8216 | PARENT (Unstable) | 32.5 | 1245 | 2435 | 8013 |

[1]Shake Flask Average of 3 Data Points (WCDW/Wt. Glucose) (WCDW = Washed Cell Dry Weight) represents percent of a theoretical yield based on 20 grams of carbon source available. Thus 4.94 grams of cell mass provides a yield of 24.7% (i.e. 4.94/20 × 100).
[2]Data is From HPLC (see Example III) for only trans 3,3'-dihydroxy-β,β-carotene-4,4'-dione
[3]μg of astaxanthin/liter calculated by multiplying the ppm by the cell concentration after 5 days of growth in Shake flask as described in Example II.

As demonstrated by PC 8166, PC 8239 and PC 8243 some of the fusion strains substantially out preform their parent strains in the production of astaxanthin. However, strain such as PC 8168, and PC 8170 also represent significant improvements over their parental strains. The parental strains PC 8117 and PC 8216 which were used in some of the fusion experiments above were unsuitable for large scale fermentation production because of their tendency to generate daughter cells which were unpigmented or lightly pigmented. The fusion strains developed from cell fusions utilizing PC 8117 and PC 8216, however, do not generate unpigmented or light colored daughter cells. Thus the fusion strains generated from unstable from highly pigmented strains provide a method of continuing strain development on highly productive *Phaffia rhodozma*.

EXAMPLE III

HPLC Pigment Analysis of Phaffia

The carotenoid pigments in *Phaffia rhodozyma* were analyzed using a normal phase HPLC system. This system uses an extraction step into n-heptane, which can be loaded directly onto the normal phase column.

0.5 ml of Phaffia culture broth was pipetted into a 2.0 ml microcentrifuge. The cells were pelleted by centrifugation in the microfuge for 5 minutes. The supernatant was decanted and glass beads (Sigma, 0.4–0.5 mm) were added to cover the remaining pellet. 300 μl of glacial acetic acid was added to the pellet, and the cells were broken by vibrating them in a mechanical shaker for 15 minutes. 1.0 ml of deionized water was added, followed by 0.5 ml of n-heptane. The carotenoids were extracted into the upper heptane phase by putting the tubes on a mechanical shaker for 10 minutes. The solvent phases were separated by centrifugution in the microfuge for 5 minutes. The tubes were stored in the cold until they were ready to be analyzed. The injection volume was 30 μl.

The HPLC system used for the quantitative analysis of astaxanthin was a Waters HPLC system, which consisted of two Model 510 pumps, a U6K manual injector, a Model 490E Programmable Multiwavelength UV/Visible Detector, a Model 680 Automated Gradient Controller, and a Model 740 Recorder/Integrator. The stationary phase used was Waters microPorosil with 10 μm packing, in a 3.9 mm × 300 mm column. The stationary phase was pretreated after initial installation by pumping a 1.0% (w/v) solution of phosphoric acid in methanol through the column for one hour at a rate of 1 ml per minute. The mobile phase was n-hexane and acetone.

Separation of all of the components of Phaffia extracts that absorb at 470 nm required the use of a gradient program. The chromatogram took 30 minutes to run, and 5 minutes to reestablish the initial solvent concentration ratio. This quantition of astaxanthin can also be accomplished using an isocratic hexane:acetone (87:13) system which takes 20 minutes to run without the need for equilibration time before the next sample is injected.

EXAMPLE IV

Astaxanthin Assays

A. Plate Assay of Astaxanthin

Modified YMA plates were streaked with cultures to be tested and incubated at 20°–22° C. aerobically. After four days, using a sterile applicator stick or loop, a patch of culture was scraped off (0.1–0.2 grams net weight) from each Modified YMA culture plate. The cells were resuspended in 1.0 ml of deionized, distilled water and placed in a 2.0 ml conical bottom microcentrifuge tube.

0.1 ml of each cell suspension was pipetted into 9.9 ml of deionized, distilled water, and the absorption was measured at 600 nm, to determine the cell concentration (in grams of washed cell dry weight per liter).

The original cell suspension (0.9 ml volume) was then pelleted by centrifugation at 14,000 g and 4° C. for 5 minutes and the supernatant was decanted. Dimethylformamide was added to bring the volume to exactly 10 ml. 0.25 grams of 450–500 micron glass beads were added and vortexed for at least 10 min. total time (with periodic cooling intervals on ice). The resulting cell debris and glass beads were pelleted by centrifugation at 14,000 g and 4° C. 0.5 ml of supernatant was removed and 1.0 ml of dimethylformamide was added. The absorption was then measured at 478 nm.

Astaxanthin concentration was calculated as follows: assume 1 μg/l of pure astaxanthin
has an $A_{478} = 176 * 10^{-6}$ with a 1 cm light path Total astaxanthin concentration of the original 1.0 ml cell suspension:

$$[\text{astaxanthin}] \text{ in } \mu g/l = \frac{A_{478} * \text{dilution factor}}{b * 176 * 10^{-6}}$$

where b = length of light path in cm (usually 1) and $$\text{dilution factor} = \frac{1.5 \text{ ml}}{0.5 \text{ ml}} * \frac{1.0 \text{ ml}}{0.9 \text{ ml}} = \frac{3}{0.9} = 3.33$$

Cellular astaxanthin concentration is then calculated as follows:

$$[\text{astaxanthin}] \text{ in } \mu g/g \text{ of cells} = \frac{\text{astaxanthin concentration } (\mu g/l)}{\text{cell concentration } (g/l)}$$

EXAMPLE V

Astaxanthin Assays

A. Spectrophotometric Method of Determination of Cell Breakage in Treated Broth

Cells from duplicate 0.2 ml treated broth samples (approximately 100 grams of cells per liter of broth) were pelleted in a table top microcentrifuge (Hermle Z 230 M, National Labnet Co, Woodbridge, N.J.) at 14,000 g for 5 min at 4° C., resuspended in 1.0 ml of deionized, distilled water and transferred to 2.0 ml conical bottom, polypropylene microcentrifuge tubes. The cells were repelleted in the polypropylene tubes by centrifugation at 14,000 g for 5 min at 4° C. and the supernatants were decanted. Acetone was added to each sample to give a volume of exactly 1.0 ml in the tube. 0.25 grams of glass beads (450–500 microns) were added to one sample and both tubes were vortexed on a Vortex, Jr. Mixer (Scientific Products, Inc) for a total of 10 min at 4° C. Glass beads and cell debris were pelleted by centrifugation at 14,000 g for 5 min at 4° C. A 0.5 ml aliquot of the supernatant was removed and added to 1.0 ml of acetone. Absorbance was measured at 478 nm. Percent breakage was determined by calculating the ratio:

$$\frac{A_{478} \text{ (no glass beads)}}{A_{478} \text{ (glass beads)}} * 100\%$$

**B. Batch-Fed Growth of *Phaffia rhodozyma* in BioLafitte**

A fresh culture of *Phaffia rhodozyma* PC 8115 was inoculated into the fermenter. This is preferably done in the following manner: A colony was picked from a plate and transferred to a 100 ml shake flask for 72 hrs. The contents of the 100 ml shake flask was then transferred to a 1000 ml shake flask for 24 hours. The contents of the 1000 ml shake flask was then transferred to the fermenter. The shake flask medium utilized comprised 0.6% yeast extract, 0.6% malt extract, 2.0% glucose. The initial fermenter volume was 10 liters with pH=5.2 and 20° C.

During the 4 day run, pH was controlled between 4.5 and 5.2 (using ammonia and phosphoric acid), the temperature was controlled between 19° C. and 21° C. (using a cooling water bath), and the % dissolved oxygen (DO) was maintained between 50% and 100% (by increasing agitation to a maximum of 1000 rpm and increasing the airflow to a maximum of 2 volumes/min. if necessary).

The fermentation was run so as to maintain a slight positive glucose (0.1% to 0.3%) for the first 100 hours. After depletion of the original glucose in the fermenter, the feed was started from a 50% glucose reservoir (1750 g glucose+1750 g H$_2$O, sterile). The initial feed rates were generally slow, but increased rapidly thereafter. Glucose concentration was monitored by LC during this process. The fermentation was then allowed to run glucose limited (glucose not detectable). The fermentation was complete 24 hours after 1750 grams of glucose had been used, provided there is no detectable glucose in the broth.

NOTE: to control foaming 3–4 drops of Mazu DF 37C was added per liter of working volume as needed.

That which is claimed is:

1. A biologically pure culture of a stable fusion strain of *Phaffia rhodozyma* which produces in the range of from about 1430 µg/g to about 1160 µg/g of astaxanthin, and from about 2350 µg/g to about 2950 µg/g of total carotenoids and provides a yield of at least 24 percent on a dry cell weight basis when cultivated under suitable growth conditions in a shake flask with a productivity of in the range of from about 4500 µg/l to about 8600 µg/l based on a 5 day shake flask assay wherein the strain is cultivated under suitable conditions to facilitate near optimum growth of said strain.

2. The strain of claim 1 wherein the strain provides a productivity of from about 7600 µg/l to about 8600 µg/l based on a 5 day shake flask assay wherein the strain is cultivated under suitable conditions to facilitate near optimum growth of said strain.

3. The strain of claim 1 wherein the strain has a percent yield in the range of from about 25 percent to about 28 percent.

4. A biologically pure culture of *Phaffia rhodozyma* strain NRRL Y-18730.

5. A biologically pure culture of *Phaffia rhodozyma* strain NRRL Y-18731.

6. A biologically pure culture of *Phaffia rhodozyma* strain NRRL Y-18732.

7. A biologically pure culture of *Phaffia rhodozyma* strain NRRL Y-18733.

8. A biologically pure culture of *Phaffia rhodozyma* strain NRRL Y-18734.

* * * * *

UNITED STATES PATENT AND TRADEMARK OFFICE
CERTIFICATE OF CORRECTION

PATENT NO. : 5,212,088
DATED : May 18, 1993
INVENTOR(S) : William D. Prevatt

It is certified that error appears in the above-identified patent and that said Letters Patent is hereby corrected as shown below:

Column 16, line 20, please delete "1160" and insert therefor ---1660---.

Signed and Sealed this

First Day of March, 1994

Attest:

BRUCE LEHMAN

*Attesting Officer*  *Commissioner of Patents and Trademarks*